United States Patent
Jan et al.

(10) Patent No.: US 8,212,097 B2
(45) Date of Patent: Jul. 3, 2012

(54) AROMATIC ALKYLATION PROCESS USING UZM-5, UZM-5P AND UZM-6 ZEOLITES

(75) Inventors: Deng-Yang Jan, Elk Grove Village, IL (US); Jaime G. Moscoso, Mount Prospect, IL (US); Raelynn M. Miller, LaGrange, IL (US); Susan C. Koster, Carpentersville, IL (US); Julio C. Marte, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/172,016

(22) Filed: Jun. 29, 2011

(65) Prior Publication Data

US 2012/0004483 A1    Jan. 5, 2012

Related U.S. Application Data

(60) Provisional application No. 61/360,707, filed on Jul. 1, 2010.

(51) Int. Cl.
*C07C 2/66*    (2006.01)

(52) U.S. Cl. ...................................................... 585/467

(58) Field of Classification Search ................... 585/467
See application file for complete search history.

(56) References Cited

U.S. PATENT DOCUMENTS

| | | |
|---|---|---|
| 3,907,711 A | 9/1975 | Riley et al. |
| 4,472,366 A | 9/1984 | Takahashi et al. |
| 4,533,649 A | 8/1985 | Ball et al. |
| 4,899,007 A | 2/1990 | Chu et al. |
| 4,921,946 A | 5/1990 | Kocal et al. |
| 5,081,323 A | 1/1992 | Innes et al. |
| 5,389,357 A | 2/1995 | Sato et al. |
| 6,388,157 B1 * | 5/2002 | Jan et al. .................. 585/467 |
| 6,613,302 B1 | 9/2003 | Moscoso et al. |
| 6,776,975 B2 | 8/2004 | Wilson et al. |
| 7,268,267 B2 | 9/2007 | Jan et al. |
| 7,578,993 B2 | 8/2009 | Lewis et al. |
| 2012/0004485 A1 | 1/2012 | Jan et al. |

OTHER PUBLICATIONS

Xu et al., Synthesis of Small Size Crystalline Offretite in TEAOH-TMABr-Al2O3-SiO2-H2O System, Journal of Fuel Chemistry and Technology, vol. 33, No. 3, Jun. 2005, pp. 351-354, language: Chinese, abstract: English.

Van Der Puil et al., Great Promise for the Petrochemical World, Abb Review, No. 2, 2000, pp. 57-62.

Jan et al.; Synthesis, Characterization, and Applictions of the New Zeolite UZM-5, Studies in Surface Science and Catalysis, vol. 154 B. 2004 Elsevier B.V., pp. 1332-1340.

* cited by examiner

*Primary Examiner* — Thuan Dinh Dang
(74) *Attorney, Agent, or Firm* — Mark R Willis

(57) ABSTRACT

A process for alkylating aromatic compounds using a family of zeolites, examples of which have been designated UZM-5, UZM-5P and UZM-6, and are represented by the empirical formula:

$$M_m^{n+}C_g^{h+}R_r^{p+}Al_{(1-x)}E_xSi_yO_z$$

where M is an alkali or alkaline earth metal, E is an optional framework element, C organic nitrogen containing cation template, and R is an organic cation crystallization template. The zeolites have at least two x-ray diffraction peaks, one at a d-spacing of 3.9±0.12 Å and one at a d-spacing 8.6±0.20 Å; a tetragonal unit cell; and a micropore volume ranging from about 0.10 cc/g to about 0.18 cc/g.

16 Claims, No Drawings

US 8,212,097 B2

AROMATIC ALKYLATION PROCESS USING UZM-5, UZM-5P AND UZM-6 ZEOLITES

CROSS-REFERENCE TO RELATED APPLICATION

This application claims the benefit of U.S. Provisional Application No. 61,360,707 which was filed on Jul. 1, 2010.

FIELD OF THE INVENTION

This invention relates to alkylation processes using a family of related crystalline aluminosilicate zeolites examples of which have been designated UZM-5, UZM-5P and UZM-6.

BACKGROUND OF THE INVENTION

Zeolites are crystalline aluminosilicate compositions which are microporous and which have a three dimensional oxide framework formed from corner sharing $AlO_2$ and $SiO_2$ tetrahedra. Numerous zeolites, both naturally occurring and synthetically prepared are used in various industrial processes. One such process is the alkylation of aromatics with olefins and especially the alkylation of benzene with ethylene or propylene. The reaction between benzene and propylene produces mostly cumene. Cumene is an important industrial compound because it is a source of phenol and acetone, which are obtained by the oxidation of cumene and subsequent acid-catalyzed decomposition of the intermediate hydroperoxide. The reaction of benzene with ethylene produces ethylbenzene, which is converted to styrene, an important raw monomer for many industrially important polymers. Acid catalysts are used to catalyze this reaction with the most common catalysts being zeolites and particularly zeolite beta.

U.S. Pat. No. 6,613,302 discloses UZM-5, UZM-5P and UZM-6 as examples of a new family of crystalline aluminosilicate zeolites. Zeolites of this family are represented by the empirical formula:

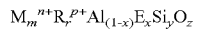

where M is an alkali or alkaline earth metal such as lithium and strontium, R is a nitrogen containing organic cation such as tetramethyl ammonium and E is a framework element such as gallium. They are also characterized by unique x-ray diffraction patterns and have catalytic properties for carrying out various hydrocarbon conversion processes.

U.S. Pat. No. 6,388,157 discloses a process for alkylation of aromatic compounds using a new family of related crystalline aluminosilicate zeolites represented by the empirical formula:

where M is an alkali or alkaline earth metal such as lithium and strontium, R is a nitrogen containing organic cation such as tetramethyl-ammonium and E is a framework element such as gallium.

U.S. Pat. No. 7,578,993 discloses a process for preparing crystalline aluminosilicate compositions involving preparing a charge density mismatch reaction mixture comprising sources of aluminum, silicon, optionally an E metal and at least one charge density mismatch (CDM) template. The CDM template is an organic nitrogen containing template, in the hydroxide form, e.g. tetraethylammonium hydroxide and is characterized in that it is incapable of inducing crystallization. To this mixture there is added a solution comprising a second templating agent termed a crystallization template (CT). The CT can be an organic template different from the CDM template, an alkali metal, an alkaline earth metal and mixtures thereof.

SUMMARY OF THE INVENTION

Applicants have found that a family of zeolites characterized by empirical formula (1) given below and having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.10 cc/g to about 0.18 cc/g provide an unexpected improvement in activity and selectivity for the alkylation of aromatics. Exemplary zeolites of the family include UZM-5, UZM-5P and UZM-6.

In an embodiment, the invention is a process for alkylating aromatic compounds comprising reacting under alkylation conditions and under at least partial liquid phase conditions an olefin with an alkylatable aromatic compound in the presence of a catalyst to provide an alkylated compound, the catalyst comprising a zeolite having a composition in the as synthesized form on an anhydrous basis in terms of mole ratios of the elements given by empirical formula (I):

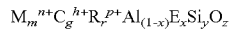

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation (2):

$$z=(m \cdot n+g \cdot h+r \cdot p+3+4 \cdot y)/2 \qquad (2)$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.10 cc/g to about 0.18 cc/g.

In an embodiment the process involves the alkylation of benzene with ethylene to produce ethylbenzene. In another embodiment, the process involves the alkylation of benzene with propylene to produce cumene.

In a further embodiment, the invention is a transalkylation process comprising reacting under transalkylation reaction conditions a polyalkylated aromatic compound with a non-alkylated aromatic compound in the presence of the zeolites described above, wherein at least one alkyl group is transferred from the polyalkylated aromatic compound to the non-alkylated aromatic compound.

DETAILED DESCRIPTION OF THE INVENTION

An essential feature of applicants' process is a zeolite having a composition on an as synthesized and anhydrous basis expressed by empirical formula (I):

$$M_m^{n+}C_g^{h+}R_r^{p+}Al_{(1-x)}E_xSi_yO_z$$

In the above equation, M represents at least one exchangeable cation and is selected from the group consisting of alkali and alkaline earth metals. Specific examples of the M cations include but are not limited to lithium, sodium, potassium, rubidium, cesium, calcium, strontium, barium, magnesium, and mixtures thereof. C is at least one organic cation, hereinafter referred to as the Charge Density Mismatch template, and is characterized in that it cannot crystallize the aluminosilicate composition from the reaction mixture without supplemental sources of crystallization inducing R ions. C is selected from the group of organic cations consisting of quaternary ammonium ions, diquaternary ammonium ions, and quaternized alkanolammonium ions. Preferred C organic cations have at least an atomic ratio of C/N>4 and preferably C/N>5, non-limiting examples include diethyldimethylammonium, tetraethylammonium, tetrapropylammonium, methyltriethylammonium, tetrabutylammonium, ethyltrimethylammonium, choline, hexamethonium, hexyltrimethylammonium, trimethylbutylammonium and trimethylcetylammonium ions. R is also at least one organic cation (different from C), and is distinguished from C in that it can induce crystallization of the aluminosilicate composition from the reaction mixture, is a higher charge density cation than C, is more likely to be incorporated into the zeolite than C, and is added in a much smaller portion to the reaction mixture than is C. R is an organic cation which is selected from the group consisting of quaternary ammonium ions, diquaternary ammonium ions, protonated amines, protonated diamines, protonated alkanolamines and quaternized alkanolammonium ions. Preferred organic cations are quaternary and diquaternary ammonium ions. Non-limiting examples of quaternary ammonium ions are tetramethyl-, ethyltrimethyl-, methyltriethyl, diethyldimethyl-, trimethylbutyl-, and trimethylpropyl-ammonium ions. Non-limiting examples of diquaternary ammonium ions are hexamethonium, pentamethonium, octamethonium, decamethonium, dimethylene bis (trimethylammonium), trimethylene bis(trimethylammonium), methylene bis(trimethylammonium) and tetramethylene bis(trimethylammonium). The value of "n" which is the weighted average valence of M varies from about 1 to about 2. The value of "h" which is the weighted average valence of C varies from about 1 to about 2. The value of "p" which is the weighted average valence of R varies from about 1 to about 2. The ratio of M to (Al+E) is represented by "m", which varies from more than 0 to about 1.2, "g" is the ratio of C to (Al+E) and varies from more than 0 to about 5, while "r" is the ratio of R to (Al+E) and varies from more than 0 to about 3, where g+r>0.2. The ratio of silicon to (Al+E) is represented by "y" which varies about 5 to about 12. E is an optional element, which when present, is tetrahedrally coordinated, is present in the framework, and is at least one element selected from the group consisting of gallium, iron, indium, chromium, titanium, zirconium, and boron. The mole fraction of E is represented by "x" and has a value from 0 to about 0.5, while "z" is the mole ratio of 0 to (Al+E) and is given by the equation (2):

$$z=(m \cdot n+g \cdot h+r \cdot p+3+4 \cdot y)/2 \qquad (2)$$

Where M is only one metal, the weighted average valence is the valence of that metal, i.e. +1 or +2. However, when more than one M metal is present, the total amount of $$M_m^{n+}=M_{m1}^{(n1)+}+M_{m2}^{(n2)+}+M_{m3}^{(n3)+}+\ldots$$

and the weighted average valence "n" is given by the equation:

$$n=(m_1 \cdot n_1+m_2 \cdot n_2+m_3 \cdot n_3+\ldots)/(m_1+m_2+m_3+\ldots)$$

Similarly, when two or more C or R cations are present, the total amount of C and R are given by the equations:

$$R_r^{p+}=R_{r1}^{(p1)+}+R_{r2}^{(p2)+}R_{r3}^{(p3)+}+\ldots$$
$$C_g^{h+}=C_{g1}^{(h1)+}+C_{g2}^{(h2)+}+C_{g3}^{(h3)+}+\ldots$$

and the weighted average valences "p" and "h" are given by the equation $$p=(r_1 \cdot p_1+r_2 \cdot p_2+r_3 \cdot p_3+\ldots)/(r_1+r_2+r_3+\ldots)$$
$$h=(g_1 \cdot h_1+g_2 \cdot h_2+g_3 \cdot h_3+\ldots)/(g_1+g_2+g_3+\ldots)$$

The sources of aluminum include but are not limited to precipitated aluminas, aluminum hydroxide, aluminum metal, aluminum salts and alumina sols. In an embodiment the aluminum source is aluminum hydroxide. Non-limiting sources of silica include but are not limited to fumed silicas, colloidal silica, and precipitated silicas. In an embodiment the silica source is colloidal silica. In another embodiment, the aluminum source is aluminum hydroxide and the silica source is colloidal silica. Sources of the E elements include but are not limited to alkali borates, boric acid, precipitated gallium oxyhydroxide, gallium sulfate, gallium nitrate, iron hydroxide, ferric sulfate, ferric chloride, chromium chloride, chromium nitrate, indium chloride, indium nitrate, titanium alkoxide, titanium chloride, zirconium alkoxide, and zirconyl chloride hydrate. As stated, the C source is required to be the hydroxide form of the organic cation. Specific examples include without limitation tetrapropylammonium hydroxide, tetraethylammonium hydroxide, methyltriethylammonium hydroxide, diethyldimethylammonium hydroxide, hexamethonium dihydroxide and ethyltrimethylammonium hydroxide. The resulting Charge Density Mismatch (CDM) reaction mixture should not be capable of crystallizing a crystalline aluminosilicate composition at the reaction temperatures at which the aluminosilicate synthesis is carried out, usually in the range of about 90° C. to about 150° C.

The CDM reaction mixture which comprises reactive sources of the desired components can be described in terms of molar ratios of the oxides by the formula:

$$bC_{2/h}O:1-dAl_2O_3:dE_2O_3:eSiO_2:fH_2O$$

"b" varies from more than 0 to about 25, "d" varies from 0 to about 0.5, "e" varies from about 5 to about 30, and "f" varies from about 10 to 5000. The CDM reaction mixture is aged with mixing at a temperature of about 50° C. to about 100° C. for a time of about 1 hour to about 5 days to provide an aged Charge Density Mismatch mixture. The CDM reaction mixture is mixed, stirred, or otherwise agitated (e.g. shaken, circulated) during this aging step. In an embodiment, the temperature during this mixing or aging step ranges from about 85° C. to about 100° C. In another embodiment, the aging time ranges from about 8 hours to about 4 days, and the aging time may range from about 12 hr to about 3 days.

To the aged CDM mixture there is admixed a crystallization inducing templating agent, R organic cation, and a source of M to provide a final reaction mixture. R and M may be premixed and added together or they may be added separately to the aged CDM mixture. This R organic cation is termed a crystallization template (CT), because it is the species that induces crystallization in the previously uncrystallizable CDM reaction mixture. The sources of R can be without limitation the halides, e.g. chlorides, carbonates, acetates or hydroxides with the hydroxides preferred. Sources of M include without limitation the halides, hydroxides, acetates etc. In an embodiment, the source of M is selected from the group of salts consisting of halide salts, nitrate salts, sulfate salts, hydroxide salts, acetates salts, and combinations thereof.

The composition of the final reaction mixture can be expressed in terms of mole ratios of the oxides of equation (3):

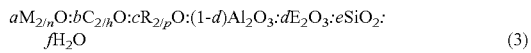

$$aM_{2/n}O:bC_{2/h}O:cR_{2/p}O:(1-d)Al_2O_3:dE_2O_3:eSiO_2: fH_2O \quad (3)$$

The level of (CT), R organic cation, added to the aged CDM mixture is given by "c", which represents the ratio of R to (Al+E) and varies from more than 0 to about 5, while "b" has a value from more than 0 to about 25, where c+b>0.2; "d" has a value from 0 to about 0.5, "e" has a value of about 5 to about 30 and "f" has a value of about 10 to about 5000. M, the alkali or alkaline earth metals are added to the aged CDM mixture at a level given by "a", which represents the mole ratio of M to (Al+E) and varies from more than 0 to about 2. Preferred values for "a" and "c" vary from about 0.1 to about 1 and most preferably from 0.1 to about 0.5, especially at Si/Al ratios less than 10. The higher values in the range for "a" and "c" are encountered at Si/Al ratios greater than 10 as Al concentrations become lower.

The resultant final reaction mixture is now reacted with mixing, stirring, or otherwise being agitated at a temperature of about 90° C. to about 150° C. and preferably at about 115° C. to about 135° C. for a time sufficient to produce the crystallized zeolite. Usually the reaction time is from about 12 hr to about 28 days and may range from about 2 days to about 14 days. In an embodiment, the reaction time ranges from more than 3 days to about 7 days. The reaction is usually carried out in a sealed vessel under autogenous pressure. After crystallization is complete, the solid product is isolated from the heterogeneous mixture by means such as filtration or centrifugation, and then washed with deionized water and dried in air at temperatures from ambient up to about 100° C.

As synthesized, the zeolites will contain some of the exchangeable or charge balancing cations in its pores. These exchangeable cations can be exchanged for other cations, or in the case of organic cations, they can be removed by heating under controlled conditions. All of these methods are well known in the art.

Specific examples of zeolites which can be prepared using methods of the instant invention include without limitation UZM-5, UZM-5P and UZM-6 which can be identified by their X-ray diffraction patterns having at least the d-spacing and relative intensities set forth in Tables A, B, and C, respectively.

TABLE A

| UZM-5 | | |
|---|---|---|
| 2-θ | d (Å) | I/I$_o$% |
| 6.31-5.89 | 14.00-15.00 | w-m |
| 7.96-7.58 | 11.10-11.65 | m-s |
| 10.40-10.01 | 8.50-8.83 | w-m |
| 12.11-11.59 | 7.30-7.63 | m |
| 16.10-15.53 | 5.50-5.70 | m-vs |
| 19.28-18.55 | 4.60-4.78 | w-m |
| 22.26-21.60 | 3.99-4.11 | m |
| 23.20-22.43 | 3.83-3.96 | w-s |
| 24.16-23.33 | 3.68-3.81 | vs |
| 30.48-29.55 | 2.93-3.02 | w-m |
| 31.94-30.92 | 2.80-2.89 | w-m |
| 44.83-43.47 | 2.02-2.08 | w |

TABLE B

| UZM-5P | | |
|---|---|---|
| 2-θ | d (Å) | I/I$_o$% |
| 6.31-5.19 | 14.00-17.00 | w-vs |
| 7.96-7.56 | 11.10-11.70 | w-m |
| 10.52-10.04 | 8.40-8.80 | m-s |
| 16.56-15.67 | 5.35-5.65 | w-m |
| 19.49-18.87 | 4.55-4.70 | w-m |
| 23.52-22.09 | 3.78-4.02 | w-vs |
| 24.03-23.39 | 3.70-3.80 | w-vs |
| 30.81-29.76 | 2.90-3.00 | w-m |
| 31.94-30.81 | 2.80-2.90 | w-m |
| 45.30-43.04 | 2.00-2.10 | w-m |

TABLE C

| UZM-6 | | |
|---|---|---|
| 2-θ | d (Å) | I/I$_o$% |
| 6.31-5.89 | 14.00-15.00 | w-m |
| 7.96-7.58 | 11.10-11.65 | m-s |
| 10.40-10.01 | 8.50-8.83 | w-m |
| 12.11-11.59 | 7.30-7.63 | m |
| 16.10-15.53 | 5.50-5.70 | m-vs |
| 19.28-18.55 | 4.60-4.78 | w-m |
| 22.26-21.60 | 3.99-4.11 | m |
| 23.20-22.43 | 3.92-4.00 | m-vs |
| 24.16-23.33 | 3.83-3.96 | w-s |
| 30.48-29.55 | 3.68-3.81 | s-vs |
| 31.94-30.92 | 2.80-2.89 | m |
| 44.83-43.47 | 2.02-2.08 | w |

In an embodiment the zeolite has a micropore volume ranging from about 0.11 cc/g to about 0.17 cc/g. In another embodiment, the zeolite has a micropore volume ranging from about 0.12 cc/g to about 0.16 cc/g and the micropore volume may range from about 0.13 cc/g to about 0.15 cc/g.

The zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m2/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. and subjected to a calcination procedure at a temperature of about 450-700° C. for a period of about 1 to about 20 hours. This treatment effects conversion of the hydrogel to the corresponding alumina matrix.

The alkylation and preferably the monoalkylation of aromatic compounds involves reacting an aromatic compound with an olefin using the above described zeolitic catalyst. The olefins which can be used in the instant process are any of those which contain from 2 up to about 20 carbon atoms. These olefins may be branched or linear olefins and either terminal or internal olefins. Preferred olefins are ethylene, propylene and those olefins which are known as detergent range olefins. Detergent range olefins are linear olefins containing from 6 up through about 20 carbon atoms which have either internal or terminal double bonds. Linear olefins containing from 8 to 16 carbon atoms are preferred and those containing from 10 up to about 14 carbon atoms are especially preferred.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also can be substituted on the alkyl chain. Although unsubstituted and mono-substituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, etc.

The particular conditions under which the monoalkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. As a practical matter the pressure normally is in the range between about 1379 kPa(g) and about 6985 kPa(g) (200-1000 psig) but usually is in a range between about 2069 kPa(g) and about 4137 kPa(g) (300-600 psig). The alkylation of the alkylatable aromatic compounds with the olefins in the C2-C20 range can be carried out at a temperature of about 60° C. to about 400° C., and preferably from about 90° C. to about 250° C., for a time sufficient to form the desired product. In a continuous process this time can vary considerably, but is usually from about 0.1 to about 3 hr-lweight hourly space velocity with respect to the olefin.

In particular, the alkylation of benzene with ethylene can be carried out at temperatures of about 160° C. to about 250° C. The alkylation of benzene by propylene at a temperature of about 90° C. to about 200° C.; and the reaction temperature to produce cumene may range from about 90° C. to about 160° C. The ratio of alkylatable aromatic compound to olefin used in the instant process will depend upon the degree of selective monoalkylation desired as well as the relative costs of the aromatic and olefinic components of the reaction mixture. For alkylation of benzene by propylene, benzene-to-olefin ratios may be as low as about 0.4 and as high as about 10, with a ratio of 1.5 to 8 being preferred. Where benzene is alkylated with ethylene a benzene-to-olefin ratio between about 0.4:1 and 8:1 is preferred. For detergent range olefins of C6-C20, a benzene-to-olefin ratio of between 5:1 up to as high as 30:1 is generally sufficient to ensure the desired monoalkylation selectivity, with a range between about 8:1 and about 20:1 even more preferred.

The zeolites of this invention can also be used to catalyze transalkylation. By "transalkylation" is meant that process where an alkyl group on one aromatic nucleus is intermolecularly transferred to a second aromatic nucleus. A preferred transalkylation process is one where one or more alkyl groups of a polyalkylated aromatic compound is transferred to a nonalkylated aromatic compound, and is exemplified by reaction of diisopropylbenzene with benzene to give two molecules of cumene. Thus, transalkylation often is utilized to add to the yield of a desired selective monoalkylation by reacting the polyalkylates invariably formed during alkylation with nonalkylated aromatic to form additional monoalkylated products. Therefore, the polyalkylated aromatic compounds may be those formed in the alkylation of alkylatable aromatic compounds with olefins as described above, and the nonalkylated aromatic compounds are benzene, naphthalene, anthracene, and phenanthrene. The reaction conditions for transalkylation are similar to those for alkylation, with temperatures being in the range of about 100° C. to about 250° C., pressures in the range of about 690 kPa(g) and about 5171 kPa(g) (100-750 psig), and the molar ratio of unalkylated aromatic to polyalkylated aromatic in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene etc.

In order to more fully illustrate the invention, the following examples are set forth. It is to be understood that the examples are only by way of illustration and are not intended as an undue limitation on the broad scope of the invention as set forth in the appended claims.

The X-ray diffraction patterns (XRD) presented in the following examples were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70° (2θ). Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "Io" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of 100×I/Io, the above designations are defined as w=0-15; m=15-60; s=60-80 and vs=80-100. In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The micropore volumes and surface areas reported in the following Examples were determined using ASTM method D4365 "Determining Micropore Volume & Zeolite Area of a Catalyst" using a Micromeritics ASAP2420 instrument or a substantially equivalent instrument. In a typical sample preparation for surface area measurement, the zeolite is first ammonium exchanged at 75° C. to lower the sodium to less than 1,000 ppm-wt $Na_2O$ on a volatile free basis. The ammonium exchanged powder is then calcined first at 350° C. and then 525° C. in flowing nitrogen, followed by air calcination at 525° C. for 5 hours, before cooling down to 100° C.

In order to more fully illustrate the invention, the following examples are set forth. It is to be understood that the examples are only by way of illustration and are not intended as an undue limitation on the broad scope of the invention as set forth in the appended claims.

EXAMPLES

Example 1 (Comparative)

An aluminosilicate reaction mixture was prepared in the following manner. Aluminum hydroxide (26.97 wt-% Al), 23.2 g, was added to 360.2 g TEAOH (35%) with vigorous stirring. To this mixture, 289.8 g colloidal silica, (Ludox AS-40, 40% $SiO_2$) was added. The reaction mixture was homogenized for 1 hr with a high-speed mechanical stirrer, and then aged in a 2-L stirred reactor overnight at 95° C. After the aging step, a solution of 21.9 g TMAOH (25%) and 4.8 g of NaOH dissolved in 700.2 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.24. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 1. A portion of the sample was calcined by ramping to 525° C. at 1° C./min in N2, holding at 525° C. in N2 for 1 hr followed by a 5 hr dwell in air, also at 525° C. The BET surface area was found to be 198 m2/g, and the micropore volume was 0.07 cc/g.

TABLE 1

| 2-θ | d (Å) | I/I$_o$ % |
|---|---|---|
| 6.07 | 14.52 | m-s |
| 7.53 | 11.71 | m |
| 10.17 | 8.68 | s |
| 11.60 | 7.62 | w |
| 15.74 | 5.62 | m |
| 18.62 | 4.76 | m |
| 20.36 | 4.35 | m |
| 21.92 | 4.05 | m |
| 22.79 | 3.89 | vs |
| 23.53 | 3.77 | s-vs |
| 26.24 | 3.39 | w |
| 26.74 | 3.33 | w |
| 27.05 | 3.29 | w |
| 30.11 | 2.96 | m |
| 30.32 | 2.94 | m |
| 30.68 | 2.91 | m |
| 31.22 | 2.86 | m |
| 32.99 | 2.71 | w |
| 43.91 | 2.05 | w |
| 52.07 | 1.75 | w |
| 53.56 | 1.70 | w |

Example 2

An aluminosilicate reaction mixture was prepared in the following manner. Aluminum hydroxide (26.97 wt-% Al), 300.3 g, was added to 3894 g TEAOH (35%) with vigorous stirring. To this mixture, 3894 g colloidal silica, (Ludox AS-40, 40% $SiO_2$) was added. The reaction mixture was homogenized for 1 hr with a high-speed mechanical stirrer, and then aged in a 5 gallon stirred reactor overnight at 95° C. After the aging step, a solution of 340 g TMAOH (25%) and 62.5 g of NaOH dissolved in 9647 g distilled water was added to the aged mixture while applying vigorous mixing. The reactor was closed and placed in a heating mantle set at 125° C., where the reaction mixture were digested for 111 hours with continuous stirring at 150 RPM. The solid product was recovered by centrifugation, washed, and dried at 100° C.

The composition of the isolated product consisted of the mole ratios Si/Al=5.76. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 2. A portion of the sample was calcined by ramping to 525° C. at 1° C./min in N2, holding at 540° C. in N2 for 1 hr followed by a 5 hr dwell in air, also at 525° C. The BET surface area was found to be 305 m2/g, and the micropore volume was 0.11 cc/g.

TABLE 2

| 2-θ | d (Å) | I/I$_o$ % |
|---|---|---|
| 5.97 | 14.77 | s |
| 7.7 | 11.47 | m |
| 10.10 | 8.75 | s |
| 11.7 | 7.55 | m |
| 15.70 | 5.63 | m |
| 18.7 | 4.74 | m |
| 20.3 | 4.37 | m |
| 21.84 | 4.06 | m |
| 22.75 | 3.90 | s-vs |
| 23.58 | 3.76 | vs |
| 26.13 | 3.40 | m |
| 29.95 | 2.98 | m |
| 31.23 | 2.86 | m |
| 32.98 | 2.71 | m |
| 44.08 | 2.05 | w |
| 52.27 | 1.74 | w |

Example 3

An aluminosilicate reaction mixture was prepared in the following manner. Aluminum hydroxide (26.97 wt-% Al), 23.6 g, was added to 360.2 g TEAOH (35%) with vigorous stirring. To this mixture, 295.4 g colloidal silica, (Ludox AS-40, 40% SiO$_2$) was added. The reaction mixture was homogenized for 1 hr with a high-speed mechanical stirrer, and then aged in a 2-L stirred reactor overnight at 95° C. After the aging step, a solution of 21.9 g TMAOH (25%) and 4.8 g of NaOH dissolved in 700.2 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.66. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 3. A portion of the sample was calcined by ramping to 525° C. at 1° C./min in N2, holding at 540° C. in N2 for 1 hr followed by a 5 hr dwell in air, also at 525° C. The BET surface area was found to be 282 m2/g, and the micropore volume was 0.11 cc/g.

TABLE 3

| 2-θ | d (Å) | I/I$_o$ % |
|---|---|---|
| 6.02 | 14.67 | s |
| 7.66 | 11.53 | m |
| 10.17 | 8.68 | s |
| 11.74 | 7.53 | w |
| 15.76 | 5.61 | m |
| 19.13 | 4.63 | w |
| 21.78 | 4.07 | m |
| 22.83 | 3.89 | vs |
| 23.56 | 3.77 | vs |
| 26.14 | 3.40 | m |
| 27.51 | 3.23 | w |
| 29.82 | 2.99 | m |
| 31.22 | 2.86 | m |
| 33.04 | 2.70 | m |
| 34.48 | 2.59 | w |
| 44.03 | 2.05 | w |

TABLE 3-continued

| 2-θ | d (Å) | I/I$_o$ % |
|---|---|---|
| 52.32 | 1.74 | w |
| 54.21 | 1.69 | w |

Example 4

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% SiO$_2$) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C. Next this material was acid treated with 1000 ml of a 5% H2SO4 solution. The initial pH of this slurry was 4, further adjustment with NH4OH solution the pH of this slurry was 7.5. This slurry was stirred at room temperature for 1 hr. the solid was recovered by filtration, washed and dry at 100 C.

The composition of the isolated product consisted of the mole ratios Si/Al=6.35. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 4. A portion of the sample was calcined by ramping to 525° C. at 1° C./min in N2, holding at 525° C. in N2 for 1 hr followed by a 5 hr dwell in air, also at 525° C. The BET surface area was found to be 348 m2/g, and the micropore volume was 0.13 cc/g.

TABLE 4

| 2-θ | d (Å) | I/I$_o$ % |
|---|---|---|
| 5.81 | 15.17 | m |
| 7.54 | 11.71 | m |
| 10.18 | 8.68 | s |
| 11.78 | 7.50 | w |
| 15.64 | 5.66 | m |
| 16.48 | 5.37 | m |
| 16.93 | 5.23 | m |
| 18.67 | 4.74 | w |
| 20.42 | 4.34 | s |
| 21.88 | 4.05 | m |
| 22.83 | 3.89 | vs |
| 23.58 | 3.76 | s |
| 26.23 | 3.39 | w |
| 27.37 | 3.25 | w |
| 28.37 | 3.14 | w |
| 29.22 | 3.05 | m |
| 29.99 | 2.97 | m |
| 30.84 | 2.89 | w |
| 31.31 | 2.85 | m |
| 31.50 | 2.83 | w |
| 33.09 | 2.70 | m |
| 33.69 | 2.65 | m |
| 34.13 | 2.62 | w |
| 41.55 | 2.17 | w |
| 44.02 | 2.05 | w |
| 52.56 | 1.73 | w |

Example 5

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% $SiO_2$) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.39. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 5. A portion of the sample was calcined by ramping to 525° C. at 2° C./min in $N_2$, holding at 525° C. in $N_2$ for 1 hr followed by a 5 hr dwell in air, also at 525° C. The BET surface area was found to be 416 m²/g, and the micropore volume was 0.14 cc/g.

TABLE 5

| 2-θ | d (Å) | I/I$_o$ % |
|---|---|---|
| 6.02 | 14.67 | m |
| 7.62 | 11.58 | m |
| 10.13 | 8.71 | s |
| 11.68 | 7.57 | m |
| 15.70 | 5.63 | m |
| 16.47 | 5.37 | m |
| 18.73 | 4.73 | m |
| 20.34 | 4.36 | w |
| 21.76 | 4.08 | m |
| 22.79 | 3.89 | s |
| 23.58 | 3.76 | vs |
| 26.22 | 3.39 | m |
| 27.48 | 3.24 | w |
| 29.94 | 2.98 | m |
| 30.76 | 2.90 | m |
| 31.28 | 2.85 | m |
| 33 | 2.71 | m |
| 34.86 | 2.57 | w |
| 43.92 | 2.05 | w |
| 52.29 | 1.74 | w |

Example 6

An aluminosilicate reaction mixture was prepared in the following manner. Aluminum hydroxide (26.97 wt-% Al), 300.3 g, was added to 3894 g TEAOH (35%) with vigorous stirring. To this mixture, 3894 g colloidal silica, (Ludox AS-40, 40% $SiO_2$) was added. The reaction mixture was homogenized for 1 hr with a high-speed mechanical stirrer, and then aged in a 5 gallon stirred reactor overnight at 95° C. After the aging step, a solution of 340 g TMAOH (25%) and 62.5 g of NaOH dissolved in 9647 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.35. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 6. A portion of the sample was calcined by ramping to 525° C. at 2° C./min in N2, holding at 525° C. in N2 for 1 hr followed by a 5 hr dwell in air, also at 525° C. The micropore volume was 0.15 cc/g.

TABLE 6

| 2-θ | d (Å) | I/I$_o$ % |
|---|---|---|
| 6.15 | 14.33 | m |
| 7.64 | 11.56 | m |
| 10.13 | 8.71 | s |
| 11.72 | 7.54 | m |
| 15.80 | 5.60 | m |
| 16.37 | 5.40 | m |
| 18.75 | 4.72 | m |
| 20.34 | 4.36 | w |
| 21.88 | 4.05 | s |
| 22.75 | 3.90 | s |
| 23.62 | 3.76 | vs |
| 24.90 | 3.57 | w |
| 26.21 | 3.39 | m |
| 26.96 | 3.30 | w |
| 27.51 | 3.23 | w |
| 30.02 | 2.97 | m |
| 30.64 | 2.91 | m |
| 31.3 | 2.85 | m |
| 33.12 | 2.70 | m |
| 34.49 | 2.59 | w |
| 44.13 | 2.05 | w |
| 52.51 | 1.74 | w |
| 54.28 | 1.68 | w |

Example 7

An aluminosilicate reaction mixture was prepared in the following manner. Aluminum hydroxide (26.97 wt-% Al), 23.2 g, was added to 360.2 g TEAOH (35%) with vigorous stirring. To this mixture, 289.8 g colloidal silica, (Ludox AS-40, 40% $SiO_2$) was added. The reaction mixture was homogenized for 1 hr with a high-speed mechanical stirrer, and then aged in a 2-L stirred reactor overnight at 95° C. After the aging step, a solution of 21.09 g TMAOH (25%) and 4.9 g of NaOH dissolved in 700.2 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.39. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 7. A portion of the sample was calcined by ramping to 525° C. at 2° C./min in N2, holding at 525° C. in N2 for 1 hr followed by a 5 hr dwell in air, also at 525° C. The BET surface area was found to be 467 m2/g, and the micropore volume was 0.16 cc/g.

TABLE 7

| 2-θ | d (Å) | I/I$_o$ % |
|---|---|---|
| 6.09 | 14.47 | m |
| 7.64 | 11.56 | m |
| 10.21 | 8.64 | s |
| 11.76 | 7.51 | m |
| 15.75 | 5.61 | m |
| 18.99 | 4.66 | m |
| 21.92 | 4.05 | s |
| 22.86 | 3.88 | vs |
| 23.72 | 3.74 | vs |
| 26.25 | 3.39 | m |
| 27.02 | 3.29 | m |
| 27.25 | 3.26 | m |
| 30.01 | 2.97 | m |
| 31.31 | 2.85 | m |
| 33.14 | 2.70 | m |
| 34.73 | 2.58 | w |
| 44.084 | 2.05 | w |
| 52.64 | 1.73 | w |
| 54.11 | 1.69 | w |

Example 8

An aluminosilicate reaction mixture was prepared in the following manner. Aluminum hydroxide (26.97 wt-% Al), 24.46 g, was added to 313.67 g TEAOH (35%) with vigorous stirring. To this mixture, 298.75 g colloidal silica, (Ludox AS-40, 40% SiO$_2$) was added. The reaction mixture was homogenized for 1 hr with a high-speed mechanical stirrer, and then aged in a 2-L stirred reactor overnight at 95° C. After the aging step, a solution of 23.05 g TMAOH (25%) and 5.04 g of NaOH dissolved in 735.03 g distilled water was added to the aged mixture while applying vigorous mixing. The reactor was closed and placed in a heating mantle set at 125° C., where the reaction mixture were digested for 135 hours with continuous stirring at 150 RPM. The solid product was recovered by centrifugation, washed, and dried at 100° C.

The composition of the isolated product consisted of the mole ratios Si/Al=5.63. Scanning Electron Microscopy (SEM) showed the crystallites to consist of clustered platelets approximately 300-500 nm across. Powder X-ray diffraction of the product showed the pattern to be consistent with that for UZM-5P. Characteristic lines in the X-ray diffraction pattern are shown in Table 8. A portion of the sample was calcined by ramping to 525° C. at 2° C./min in N2, holding at 525° C. in N2 for 1 hr followed by a 5 hr dwell in air, also at 525° C. The BET surface area was found to be 412 m2/g, and the micropore volume was 0.17 cc/g.

TABLE 8

| 2-θ | d (Å) | I/I$_o$ % |
|---|---|---|
| 5.66 | 15.59 | m |
| 7.66 | 11.53 | m |
| 10.12 | 8.73 | s |
| 11.74 | 7.53 | m |
| 15.74 | 5.62 | m |
| 18.9 | 4.69 | m |
| 20.32 | 4.36 | w |
| 21.76 | 4.08 | s |
| 22.70 | 3.91 | s |
| 23.5 | 3.78 | vs |
| 26.23 | 3.39 | m |
| 26.89 | 3.31 | w |
| 27.43 | 3.24 | w |
| 29.85 | 2.98 | m |
| 31.3 | 2.85 | m |
| 33.02 | 2.71 | m |
| 37.83 | 2.37 | w |
| 43.88 | 2.06 | w |
| 52.37 | 1.74 | w |
| 54.31 | 1.68 | w |

Example 9

An aluminosilicate reaction mixture was prepared in the following manner. Aluminum hydroxide (26.97 wt-% Al), 23.6 g, was added to 305.7 g TEAOH (35%) with vigorous stirring. To this mixture, 295 g colloidal silica, (Ludox AS-40, 40% SiO$_2$) was added. The reaction mixture was homogenized for 1 hr with a high-speed mechanical stirrer, and then aged in a 2-L stirred reactor overnight at 95° C. After the aging step, a solution of 26.7 g TMAOH (25%) and 4.9 g of NaOH dissolved in 744.1 g distilled water was added to the aged mixture while applying vigorous mixing. The reactor was closed and placed in a heating mantle set at 125° C., where the reaction mixture were digested for 96 hours with continuous stirring at 150 RPM. The solid product was recovered by centrifugation, washed, and dried at 100° C.

The composition of the isolated product consisted of the mole ratios Si/Al=5.84. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 9. A portion of the sample was calcined by ramping to 525° C. at 1° C./min in N2, holding at 525° C. in N2 for 1 hr followed by a 5 hr dwell in air, also at 525° C. The BET surface area was found to be 453 m2/g, and the micropore volume was 0.17 cc/g.

TABLE 9

| 2-θ | d (Å) | I/I$_o$ % |
|---|---|---|
| 5.9 | 14.96 | m |
| 7.58 | 11.65 | m |
| 10.06 | 8.78 | s |
| 11.58 | 7.63 | m |
| 15.63 | 5.66 | m |
| 16.30 | 5.43 | m |
| 18.73 | 4.73 | m |
| 20.28 | 4.37 | w |
| 21.84 | 4.06 | m |
| 22.68 | 3.91 | s |
| 23.48 | 3.78 | vs |
| 26.15 | 3.40 | m |
| 27.00 | 3.29 | w |
| 27.44 | 3.24 | w |
| 29.88 | 2.98 | m |
| 30.72 | 2.90 | m |
| 31.22 | 2.86 | m |
| 32.92 | 2.71 | m |
| 34.31 | 2.61 | w |
| 36.44 | 2.46 | w |
| 43.92 | 2.05 | w |
| 52.40 | 1.74 | w |
| 53.91 | 1.69 | w |

Example 10 (Comparative)

An aluminosilicate reaction mixture was prepared in the following manner.

Aluminum hydroxide (26.97 wt-% Al), 37.5 g, was added to 481.2 g TEAOH (35%) with vigorous stirring. To this mixture, 464.3 g colloidal silica, (Ludox AS-40, 40% $SiO_2$) was added. The reaction mixture was homogenized for 1 hr with a high-speed mechanical stirrer, and then aged in a 2-L stirred reactor overnight at 95° C. After the aging step, a solution of 35 g TMAOH (25%) and 7.7 g of NaOH dissolved in 374.1 g distilled water was added to the aged mixture while applying vigorous mixing. The reactor was closed and placed in a heating mantle set at 125° C., where the reaction mixture were digested for 72 hours with continuous stirring at 100 RPM. The solid product was recovered by centrifugation, washed, and dried at 100° C.

The composition of the isolated product consisted of the mole ratios Si/Al=6.13. Scanning Electron Microscopy (SEM) showed the crystallites to consist of clustered platelets approximately 300-500 nm across. Powder X-ray diffraction of the product showed the pattern to be consistent with that for UZM-5. Characteristic lines in the X-ray diffraction pattern are shown in Table 10. A portion of the sample was calcined by ramping to 525° C. at 1° C./min in N2, holding at 525° C. in N2 for 1 hr followed by a 5 hr dwell in air, also at 525° C. The BET surface area was found to be 597 m2/g, and the micropore volume was 0.2 cc/g.

TABLE 10

| 2-θ | d (Å) | I/$I_o$ % |
|---|---|---|
| 6 | 14.71 | m |
| 7.72 | 11.44 | m |
| 10.13 | 8.71 | m-s |
| 11.82 | 7.48 | m |
| 15.78 | 5.61 | m |
| 16.46 | 5.38 | m |
| 18.8 | 4.71 | m |
| 20.36 | 4.35 | m |
| 21.28 | 4.17 | m |
| 21.89 | 4.05 | s |
| 22.74 | 3.90 | s |
| 23.56 | 3.77 | vs |
| 25.02 | 3.55 | w |
| 26.21 | 3.39 | m |
| 27.16 | 3.28 | m |
| 28.92 | 3.08 | w |
| 30.04 | 2.97 | m |
| 30.74 | 2.90 | w |
| 31.26 | 2.85 | m |
| 33.02 | 2.71 | m |
| 34.34 | 2.60 | w |
| 44.12 | 2.05 | w |
| 52.44 | 1.74 | w |
| 53.96 | 1.69 | w |

Example 11

Procedure for Catalyst Preparations

Zeolite powders from each of Examples 1 through 10 were formulated into separate catalysts as 70/30 w/w zeolite/alumina of 1/16" diameter cylinders and dried in a box oven with air flow at 250° C. for 4 hours. The dried extrudates were then $NH_4NO_3$ exchanged with a weight ratio of 1:1:10 catalyst: $NH_4NO_3$:de-ionized water. Catalyst and solution were combined in a beaker and heated to 55° C. on a hot plate. Total contact time was 90 minutes and occasional stirring with a spatula was applied to ensure uniform contact. The exchange solution was drained and the extrudates were typically rinsed four times with 800 ml of de-ionized water. The entire $NH_4NO_3$ exchange procedure was repeated. The rinsed catalyst was transferred to a flat evaporating dish and dried at 120° C. overnight in a box oven with air flow.

Calcination of the catalyst was done in a stainless steel mesh basket in a box oven to ensure adequate flow through the catalyst bed. Calcination was done in a box oven first under nitrogen flow by raising the temperature at 1° C./min to 250° C. and hold for 2 hrs, then raising the temperature further to 350° C. and hold for 2 hrs; and then again raising the temperature at 1° C./min to 525° C. and hold 1 hr. Thereafter, the gas flow is switched to air, and continue holding at 525° C. for an additional 4 hrs. At the end of 4 hrs hold at 525° C. in the flowing air, the oven is cooled to 110° C. before unloading.

Example 12

Catalyst Test

The catalysts prepared from the zeolites of Examples 1-10 were tested in a benzene alkylation test as follows. 40 ml of catalyst is loaded into 5/8" i.d. differential reactor. The catalyst is pre-dried in hot benzene at 250° C. until the effluent dew point is below −30° C. at 700 psig pressure. The reactor is then cooled down to attain target inlet temperatures. Once the target inlet temperature is achieved, ethylene feed is introduced at a rate to achieve a benzene to ethylene molar ratio of molar ratio of 10.5 at an inlet temperature of 200° C. Thereafter, the test condition is moved to a benzene to ethylene ratio of 7.0; first at an inlet temperature of 200 and then 180° C. The olefin WHSV is approximately 0.4 $hr^{-1}$. The activity is determined by the location of the maximum temperature measured as distance from the inlet of the catalyst bed to the maximum temperature location. The closer the maximum temperature location is to the inlet temperature, the more active the catalyst is. The product selectivity is calculated based on the composition of product effluent determined by on-line GC.

The activity and selectivity of catalyst Examples 1-10 are summarized in Tables 11-13 with the zeolite micropore volumes and BET surface area properties. Unexpectedly, the zeolites having a micropore volume ranging from about 0.10 cc/g to about 0.18 cc/g exhibit better selectivity and activity relative to comparative Examples 1 and 10 having micropore volumes of 0.07 cc/g and 0.20 cc/g, respectively. Further, it is surprising to see the data exhibit maximum values of activity and selectivity within the micropore volume range of about 0.10 cc/g to about 0.18 cc/g. The performance continues to improve in the micropore volume of about 0.11 cc/g to about 0.17 cc/g, and between about 0.12 cc/g to about 0.16 cc/g, and most beneficially between about 0.13 cc/g to about 0.15 cc/g.

TABLE 11

| | Target B/E = 10.5, Inlet = 200° C. | | | | | |
|---|---|---|---|---|---|---|
| Example # | Micropore Volume ml/g | BET Surface Area m2/g | B/E, Actual mole ratio | Activity, Max. Temp. Location, in. | EB Selectivity | Total Alkylate Selectivity |
| 1 (comp) | 0.07 | 198 | 9.4 | 4.8 | 92.0 | 98.8 |
| 2 | 0.11 | 305 | 9.3 | 1.8 | 91.7 | 99.1 |
| 3 | 0.11 | 282 | 9.1 | 2.3 | 92.0 | 99.0 |
| 4 | 0.13 | 348 | 10.1 | 1.3 | 92.5 | 99.5 |
| 5 | 0.14 | 416 | 8.8 | 1.0 | 90.8 | 99.2 |
| 6 | 0.15 | — | 9.8 | 1.5 | 92.7 | 99.4 |
| 7 | 0.16 | 467 | 8.3 | 1.9 | 91.4 | 99.2 |
| 7 | 0.16 | 467 | 9.5 | 2.5 | 92.2 | 99.1 |
| 8 | 0.17 | 412 | 9.7 | 2.5 | 93.6 | 99.4 |
| 9 | 0.17 | 453 | 9.7 | 3.3 | 93.1 | 99.2 |
| 10 (comp) | 0.20 | 597 | 9.6 | 3.2 | 93.3 | 99.0 |

TABLE 12

Target B/E = 7, Inlet = 200° C.

| Example # | Micropore Volume ml/g | BET Surface Area m2/g | B/E, Actual mole ratio | Activity, Max. Temp. Location, in. | EB Selectivity | Total Alkylate Selectivity |
|---|---|---|---|---|---|---|
| 1 (comp) | 0.07 | 198 | 7.2 | 5.8 | 90.4 | 98.5 |
| 2 | 0.11 | 305 | 6.9 | 2.0 | 88.3 | 99.0 |
| 3 | 0.11 | 282 | 6.8 | 3.3 | 89.5 | 99.0 |
| 4 | 0.13 | 348 | 6.6 | 1.7 | 88.9 | 99.4 |
| 5 | 0.14 | 416 | 6.4 | 1.2 | 86.7 | 99.2 |
| 6 | 0.15 | — | 6.3 | 2.0 | 88.0 | 99.4 |
| 7 | 0.16 | 467 | 6.1 | 2.0 | 88.5 | 99.2 |
| 7 | 0.16 | 467 | 5.9 | 3.0 | 87.5 | 99.0 |
| 8 | 0.17 | 412 | 6.3 | 3.0 | 89.7 | 99.4 |
| 9 | 0.17 | 453 | 6.1 | 5.7 | 89.4 | 98.7 |
| 10 (comp) | 0.20 | 597 | 6.3 | 4.8 | 89.4 | 98.9 |

TABLE 13

Target B/E = 7, Inlet = 180° C.

| Example # | Micropore Volume ml/g | BET Surface Area m2/g | B/E, Actual mole ratio | Activity, Max. Temp. Location, in. | EB Selectivity | Total Alkylate Selectivity |
|---|---|---|---|---|---|---|
| 1 (comp) | 0.07 | 198 | 7.7 | 8.8 | 93.8 | 97.8 |
| 2 | 0.11 | 305 | 6.9 | 4.0 | 90.4 | 99.1 |
| 3 | 0.11 | 282 | 6.9 | 6.0 | 91.5 | 99.0 |
| 4 | 0.13 | 348 | 6.6 | 2.8 | 90.0 | 99.3 |
| 5 | 0.14 | 416 | 6.4 | 2.2 | 88.7 | 99.1 |
| 6 | 0.15 | — | 6.2 | 3.0 | 90.0 | 99.4 |
| 7 | 0.16 | 467 | 6.2 | 4.2 | 90.7 | 99.2 |
| 7 | 0.16 | 467 | 6.1 | 5.0 | 89.5 | 99.1 |
| 8 | 0.17 | 412 | 6.4 | 6.3 | 92.0 | 99.3 |
| 9 | 0.17 | 453 | 7.1 | 7.3 | 94.2 | 98.0 |
| 10 (comp) | 0.20 | 597 | 6.9 | 10.0 | 93.1 | 98.0 |

The invention claimed is:

1. A process for alkylating aromatic compounds comprising reacting under alkylation conditions and under at least partial liquid phase conditions an olefin with an alkylatable aromatic compound in the presence of a catalyst to provide an alkylated compound, the catalyst comprising a zeolite having a composition in the as synthesized form on an anhydrous basis in terms of mole ratios of the elements given by empirical formula:

$$M_m^{n+}C_g^{h+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m \cdot n+g \cdot h+r \cdot p+3+4 \cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.11 cc/g to about 0.17 cc/g.

2. The process of claim 1 wherein the zeolite has a X-ray powder diffraction pattern which contains at least the d-spacings and relative intensities of one of Tables A, B, and C.

3. The process of claim 1 wherein C is selected from the group of organic nitrogen containing cations consisting of tetrapropylammonium, tetraethylammonium, diethyldimethylammonium, methyltriethylammonium, tetrabutylammonium, ethyltrimethylammonium, choline, hexamethonium, hexyltrimethylammonium, trimethylbutylammonium, trimethylcetylammonium, and mixtures thereof.

4. The process of claim 1 wherein R is selected from the group of quaternary ammonium ions consisting of tetramethylammonium, ethyltrimethylammonium, diethyldimethylammonium, methyltriethylammonium, trimethylbutylammonium, trimethylpropylammonium, and mixtures thereof.

5. The process of claim 1 wherein M is at least one metal selected from the group consisting of lithium, cesium, sodium, potassium, strontium, barium, calcium, and magnesium, and R is a quaternary ammonium ion.

6. The process of claim 5 wherein M is sodium and the R comprises a tetramethylammonium ion.

7. The process of claim 1 wherein M is a mixture of an alkali metal and an alkaline earth metal and R is a quaternary ammonium cation.

8. The process of claim 1 wherein M comprises sodium, C comprises a tetraethylammonium cation, and R comprises a tetramethylammonium cation.

9. The process of claim 1 further comprising E wherein "x" has a value from about 0.05 to about 0.5.

10. The process of claim 9 wherein E comprises at least one of gallium, iron, boron, and titanium.

11. The process is a monoalkylation process.

12. The process of claim 1 where the olefin contains from 2 up to about 20 carbon atoms.

13. The process of claim 1 where the alkylatable aromatic compound is selected from the group consisting of benzene, naphthalene, anthracene, phenanthrene, and substituted derivatives thereof.

14. The process of claim 1 where the reaction conditions include a temperature from about 60° C. to about 400° C. and a reaction pressure varies from about 1379 kPa(g) to about 6985 kPa(g).

15. A process for preparing cumene by the alkylation of benzene with propylene comprising reacting propylene with benzene at reaction conditions including a pressure sufficient to maintain at least a partial liquid phase in the presence of a catalyst comprising a zeolite having a composition in the as synthesized form on an anhydrous basis in terms of mole ratios of the elements given by the empirical formula $$M_m^{n+}C_g^{h+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m \cdot n+g \cdot h+r \cdot p+3+4 \cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.11 cc/g to about 0.17 cc/g.

16. A process for preparing ethylbenzene by the alkylation of benzene with ethylene comprising reacting ethylene with benzene at reaction conditions including a pressure sufficient to maintain at least a partial liquid phase in the presence of a catalyst comprising a zeolite having a composition in the as synthesized form on an anhydrous basis in terms of mole ratios of the elements given by the empirical formula $$M_m^{n+}C_g^{h+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from more than 0 to about 1.2, C is at least one organic nitrogen containing cation, having C/N>4 and characterized in that it is a charge density mismatch template, selected from the group consisting of quaternary ammonium ions, diquaternary ammonium ions, and quaternized alkanolammonium ions, "g" is the mole ratio of C to (Al+E) and varies from more than 0 to about 5, R is at least one crystallization-inducing organic cation which differs from C and is selected from the group consisting of quaternary ammonium ions, diquaternary ammonium ions, protonated amines, protonated diamines, protonated alkanolamines and quaternized alkanolammonium ions, "r" is the mole ratio of R to (Al+E) and has a value from more than 0 to about 3, where g+r>0.2, "n" is the weighted average valence of M and has a value of about 1 to about 2, "h" is the weighted average valence of C and has a value of about 1 to about 2, "p" is the weighted average valence of R and has a value of about 1 to about 2, E is an element selected from the group consisting of gallium, iron, boron, indium, chromium, titanium, zirconium, and mixtures thereof, "x" is the mole fraction of E and has a value from 0 to about 0.5, "y" is the mole ratio of Si to (Al+E) and varies from about 5 to about 12; "z" is the mole ratio of O to (Al+E) and has a value determined by the equation $$z=(m \cdot n+g \cdot h+r \cdot p+3+4 \cdot y)/2$$

the zeolite having (i) at least two x-ray diffraction peaks, one at a d-spacing of 3.9±0.12 Å and one at a d-spacing 8.6±0.20 Å; (ii) a tetragonal unit cell; and (iii) a micropore volume ranging from about 0.11 cc/g to about 0.17 cc/g.

* * * * *